(12) United States Patent
Senn et al.

(10) Patent No.: US 10,933,224 B2
(45) Date of Patent: Mar. 2, 2021

(54) METHODS AND DEVICES FOR DELIVERING DRUGS USING DRUG-DELIVERY OR DRUG-COATED GUIDEWIRES

(71) Applicant: Lake Region Medical, Inc., Chaska, MN (US)

(72) Inventors: Andrew Senn, Minneapolis, MN (US); Erik Sorensen, Minneapolis, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 176 days.

(21) Appl. No.: 16/166,324

(22) Filed: Oct. 22, 2018

(65) Prior Publication Data

US 2019/0054278 A1  Feb. 21, 2019

Related U.S. Application Data

(63) Continuation of application No. 15/173,754, filed on Jun. 6, 2016, now abandoned, which is a continuation
(Continued)

(51) Int. Cl.
*A61M 25/09* (2006.01)
*A61K 9/00* (2006.01)
(Continued)

(52) U.S. Cl.
CPC .......... *A61M 25/09* (2013.01); *A61K 9/0019* (2013.01); *A61K 9/0024* (2013.01); *A61K 9/0092* (2013.01); *A61K 9/127* (2013.01); *A61L 31/146* (2013.01); *A61L 31/148* (2013.01); *A61L 31/16* (2013.01); *A61L 31/18* (2013.01); *A61L 2300/606* (2013.01);
(Continued)

(58) Field of Classification Search
CPC .. A61M 25/0074; A61M 25/04; A61M 25/09; A61M 2025/0024; A61M 2025/0057; A61M 2025/0079; A61M 2025/09008–09191
See application file for complete search history.

(56) References Cited

U.S. PATENT DOCUMENTS 3,108,595 A * 10/1963 Overment ............. A61M 25/04
   604/105
3,568,659 A * 3/1971 Karnegis ............. A61M 1/1072
   600/18

(Continued)

OTHER PUBLICATIONS

International Search Report and Written Opinion, PCT App. No. PCT/US2010/042620, dated Mar. 10, 2011.

*Primary Examiner* — Kami A Bosworth
(74) *Attorney, Agent, or Firm* — Michael F. Scalise

(57) ABSTRACT

The present invention relates to a method of delivering drugs having e.g., anti-proliferative activity in the vascular, preferably, the cardiovascular, system locally or systematically using an at least partially drug-coated guidewire. The drug-coated guidewire, particularly an expansion member or portion thereof, is brought into contact with the target tissue or in circulation and the drugs are quickly released into the area surrounding the device in a short time after the contact step. Once the therapeutic drugs are released, they are quickly and effectively absorbed by the surrounding cells or circulation.

20 Claims, 8 Drawing Sheets

Related U.S. Application Data of application No. 12/506,499, filed on Jul. 21, 2009, now abandoned.

(51) Int. Cl.
*A61K 9/127* (2006.01)
*A61L 31/14* (2006.01)
*A61L 31/16* (2006.01)
*A61L 31/18* (2006.01)
*A61M 25/00* (2006.01)

(52) U.S. Cl.
CPC ............... *A61M 2025/0057* (2013.01); *A61M 2025/09008* (2013.01); *A61M 2025/09083* (2013.01); *A61M 2025/09091* (2013.01); *A61M 2025/09133* (2013.01); *A61M 2025/09166* (2013.01); *A61M 2025/09175* (2013.01); *A61M 2025/09183* (2013.01)

(56) References Cited

U.S. PATENT DOCUMENTS

| | | |
|---|---|---|
| 4,793,350 A * | 12/1988 | Mar ................. A61M 25/0097 604/103.1 |
| 4,838,857 A | 6/1989 | Strowe et al. |
| 4,846,174 A | 7/1989 | Willard et al. |
| 4,848,342 A * | 7/1989 | Kaltenbach ........... A61M 29/02 606/198 |
| 4,903,826 A | 2/1990 | Pearce |
| 4,921,757 A | 5/1990 | Wheatley et al. |
| 4,936,832 A | 6/1990 | Vaillancourt et al. |
| 5,002,560 A | 3/1991 | Machold et al. |
| 5,112,305 A | 5/1992 | Barath et al. |
| 5,265,622 A | 11/1993 | Barbere |
| 5,304,121 A | 4/1994 | Sahatjian et al. |
| 5,409,455 A | 4/1995 | Belden |
| 5,421,826 A | 6/1995 | Crocker et al. |
| 5,523,092 A | 6/1996 | Hanson et al. |
| 5,540,707 A | 7/1996 | Ressemann et al. |
| 5,569,197 A | 10/1996 | Helmus et al. |
| 5,571,086 A | 11/1996 | Kaplan et al. |
| 5,603,694 A | 2/1997 | Brown et al. |
| 5,674,192 A | 10/1997 | Sahatjian et al. |
| 5,681,281 A | 10/1997 | Vigil et al. |
| 5,709,874 A | 1/1998 | Hanson et al. |
| 5,713,863 A | 2/1998 | Vigil et al. |
| 5,718,711 A | 2/1998 | Berenstein et al. |
| 5,746,716 A | 5/1998 | Vigil et al. |
| 5,766,192 A * | 6/1998 | Zacca ............ A61B 17/320725 606/159 |
| 5,772,629 A | 6/1998 | Kaplan et al. |
| 5,776,100 A | 7/1998 | Forman |
| 5,779,673 A | 7/1998 | Roth et al. |
| 5,795,318 A | 8/1998 | Wang et al. |
| 5,800,408 A | 9/1998 | Strauss et al. |
| 5,855,563 A | 1/1999 | Kaplan et al. |
| 5,873,852 A | 2/1999 | Vigil et al. |
| 5,925,016 A | 7/1999 | Chornenky et al. |
| 5,928,203 A | 7/1999 | Davey et al. |
| 5,954,706 A | 9/1999 | Sahatjian et al. |
| 5,997,487 A | 12/1999 | Kolehmainen et al. |
| 6,053,900 A | 4/2000 | Brown et al. |
| 6,060,454 A | 5/2000 | Duhaylongsod |
| 6,066,158 A | 5/2000 | Engelson et al. |
| 6,077,256 A | 6/2000 | Mann |
| 6,102,903 A | 8/2000 | Tremulis |
| 6,102,904 A | 8/2000 | Vigil et al. |
| 6,120,483 A | 9/2000 | Davey et al. |
| 6,127,410 A | 10/2000 | Duhaylongsod |
| 6,152,141 A | 11/2000 | Stevens et al. |
| 6,183,461 B1 | 2/2001 | Matsuura et al. |
| 6,283,951 B1 | 9/2001 | Flaherty et al. |
| 6,347,247 B1 | 2/2002 | Dev et al. |
| 6,369,039 B1 | 4/2002 | Palasis et al. |
| 6,379,373 B1 | 4/2002 | Sawhney et al. |
| 6,398,758 B1 | 6/2002 | Jacobsen et al. |
| 6,436,077 B1 | 8/2002 | Davey et al. |
| 6,436,091 B1 | 8/2002 | Harper et al. |
| 6,485,500 B1 | 11/2002 | Kokish et al. |
| 6,514,236 B1 | 2/2003 | Stratienko et al. |
| 6,537,241 B1 | 3/2003 | Odland et al. |
| 6,569,147 B1 | 5/2003 | Evans et al. |
| 6,602,241 B2 | 8/2003 | Makower et al. |
| 6,635,027 B1 | 10/2003 | Cragg et al. |
| 6,645,176 B1 | 11/2003 | Christenson et al. |
| 6,685,648 B2 | 2/2004 | Flaherty et al. |
| 6,692,458 B2 | 2/2004 | Forman et al. |
| 6,711,436 B1 | 3/2004 | Duhaylongsod et al. |
| 6,740,331 B1 | 5/2004 | Bates et al. |
| 6,890,295 B2 | 5/2005 | Michels et al. |
| 6,918,869 B2 | 7/2005 | Shaw et al. |
| 6,951,557 B2 | 10/2005 | Ellis et al. |
| 6,997,947 B2 | 2/2006 | Walak et al. |
| 7,059,330 B1 | 6/2006 | Makower et al. |
| 7,166,280 B2 | 1/2007 | Franco et al. |
| 7,191,018 B2 | 3/2007 | Gielen et al. |
| 7,232,425 B2 | 6/2007 | Sorenson et al. |
| 7,357,794 B2 | 4/2008 | Lamson et al. |
| 7,473,242 B2 | 1/2009 | Donovan et al. |
| 7,488,313 B2 | 2/2009 | Segal et al. |
| 7,488,314 B2 | 2/2009 | Segal et al. |
| 7,517,342 B2 | 4/2009 | Scott et al. |
| 7,519,338 B2 | 4/2009 | Hausdorf et al. |
| 7,519,417 B2 | 4/2009 | Ferguson et al. |
| 8,147,534 B2 * | 4/2012 | Berez ............. A61B 17/12022 623/1.11 |
| 2002/0151823 A1 * | 10/2002 | Miyata ................. A61M 25/09 600/585 |
| 2002/0173817 A1 * | 11/2002 | Kletschka ............ A61B 17/221 606/194 |
| 2003/0100887 A1 | 5/2003 | Scott et al. |
| 2003/0163064 A1 | 8/2003 | Vrba et al. |
| 2004/0220511 A1 | 11/2004 | Scott et al. |
| 2004/0260333 A1 | 12/2004 | Dubrul et al. |
| 2005/0043680 A1 | 2/2005 | Segal et al. |
| 2005/0085847 A1 | 4/2005 | Galdonik et al. |
| 2005/0182437 A1 | 8/2005 | Bonnette et al. |
| 2005/0251246 A1 | 11/2005 | Dubrul et al. |
| 2006/0004323 A1 | 1/2006 | Chang et al. |
| 2007/0198048 A1 | 8/2007 | Behan et al. |
| 2008/0058730 A1 | 3/2008 | Melsheimer et al. |
| 2008/0125634 A1 | 5/2008 | Ryan et al. |
| 2008/0237028 A1 | 10/2008 | Kislev et al. |
| 2008/0255510 A1 | 10/2008 | Wang et al. |
| 2008/0306499 A1 * | 12/2008 | Katoh .................. A61B 17/22 606/159 |
| 2009/0069789 A1 | 3/2009 | Freyman et al. |
| 2009/0076448 A1 | 3/2009 | Consigny et al. |
| 2009/0318947 A1 | 12/2009 | Garcia et al. |

* cited by examiner

METHODS AND DEVICES FOR DELIVERING DRUGS USING DRUG-DELIVERY OR DRUG-COATED GUIDEWIRES

CROSS-REFERENCE TO RELATED APPLICATIONS

This application is a continuation of U.S. patent application Ser. No. 15/173,754, filed on Jun. 6, 2016, now abandoned, with is a continuation of U.S. patent application Ser. No. 12/506,499, filed on Jul. 21, 2009, now abandoned.

FIELD OF THE INVENTION

The present invention relates to the field of medicinal devices and their use in delivering drugs or agents (including biological substances such as cells) to a particular tissue or body lumen for local or systemic effect. In general, the present invention relates to percutaneous transluminal devices and to methods for treating obstructed (sclerotic) vessel lumina in humans. In particular, this invention relates to a low-profile guidewire drug delivery apparatus and methods for using a guidewire having an expansion member on which there is disposed a therapeutic agent. In one aspect the present invention dilates an obstruction within a vessel while simultaneously or subsequently delivering a specified therapeutic agent or medicament dose to or adjacent to the dilatation site.

BACKGROUND OF THE INVENTION

It has become increasingly common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a guidewire, a cannula or the like.

Vascular disease, particularly cardiovascular disease, is commonly accepted as being one of the most serious health risks facing our society today. Diseased and obstructed coronary arteries can restrict the flow of blood to the heart and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, percutaneous methods are available for treating cardiovascular disease. For example, percutaneous transluminal angioplasty (PTCA) balloons or excising devices (atherectomy) are used to remodel or debulk diseased vessel segments. A further treatment method involves percutaneous, intraluminal installation of expandable, tubular scaffolds or stents or prostheses in sclerotic lesions.

Exposure, however, to a medical device which is implanted or inserted into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to implanted or temporary treatment whether introduced by an operation or by a minimally invasive technique, include cell proliferation which can lead to hyperplasia, occlusion of blood vessels, platelet aggregation, rejection of artificial organs, calcification, and impairment of device function.

For example, when a medical device is introduced into and manipulated through the vascular system, the blood vessel walls can be disturbed or injured. Clot formation or thrombosis, and/or cell proliferation often results at the injured site, causing stenosis or "restenosis" (i.e., closure) of the blood vessel. Additionally, if the medical device is left within the patient for an extended period of time, thrombus may form on the device itself with subsequent cell proliferation, again causing restenosis. As a result, the patient is placed at risk of a variety of complications, including heart attack or other ischemic disease, pulmonary embolism, and stroke. Thus, the use of such a medical device can entail the risk of precisely the problems that its use was intended to ameliorate.

Restenosis is the formation of new blockages at the site of the angioplasty or stent placement or the anastamosis of the bypass. There are two major mechanisms for restenosis. The first is by thrombosis, or blood clotting, at the site of treatment. The risk of thrombosis is the greatest immediately after angioplasty, because the resultant tissue trauma tends to trigger blood clotting. This form of restenosis is greatly reduced by using anti-clotting drugs both during and after the procedure.

The second form of restenosis is tissue growth at the site of treatment. This form of restenosis, a hyperproliferation of the vascular smooth muscle cells that forms a layer in the wall of a blood vessel, tends to occur during the first three to six months after the procedure, and is not prevented by anti-clotting drugs. This form of restenosis can be thought of as resulting from exuberant or overly aggressive tissue healing and regeneration after the trauma of angioplasty and/or stent placement.

To reduce adverse effects caused by implanted medical devices, such as restenosis, pharmaceuticals, such as anticoagulants and antiproliferation drugs, have been administered in or on stents or balloon catheters. These methods require release of the active ingredients slowly. Indeed, prior art therapeutic methods generally include slow controlled agent release.

Heretofore, various devices have been disclosed which may be used to deliver a therapeutic agent or medicament to a blood vessel while undergoing angioplasty. Balloon angioplasty catheters have been used to place and deliver a various therapeutic agents or medicaments within human vessels. For example, in U.S. Pat. Nos. 5,112,305, 5,746,716, 5,304,121, 5,674,192, 5,954,706, 5,569,197, 7,519,338, 7,488,314, 7,473,242, 5,681,281, 5,873,852, 5,713,863, 6,997,947, 7,519,418, 7,517,342, and 6,102,904 disclose and claim balloon/catheter systems for delivering a drug into an arterial segment, the disclosures of each said patents being incorporated by reference herein in their entireties.

Alternatively, a standard angioplasty balloon may be coated with a polymeric material which is then used to bond certain medicaments or therapeutic agents. These agents are then delivered to the desired therapeutic site by inflation of the balloon and diffusion of the medicament or therapeutic agent into the vessel wall. Only limited quantities of therapeutic agents can be delivered because of "wash-out" of the drug into the circulation during balloon placement and due to the limited time the inflated balloon can be left in place due to ischemia caused by the balloon.

In general, it is an object of the present invention to provide a guidewire-based dilatation device and method which is capable of dilating an obstruction within a vascular segment while simultaneously delivering a therapeutic agent or medicament to the vessel segment.

Another object of the invention is to provide a guidewire-based device that can control the release or diffusion of a medicament or therapeutic agent to minimize potential systemic affects and maximize the diffusion or delivery of the medicament or therapeutic agent to the site of treatment while permitting substantially uninterrupted vascular fluid, e.g., blood, flow.

Another object of the invention is to provide a device that is not susceptible to structural damage (e.g., balloon rupture) and subsequent release of therapeutic agents or drug materials into the vasculature.

BRIEF SUMMARY OF THE INVENTION

Briefly, in one aspect, the present invention is guidewire-based methods and apparatuses or devices of delivering drugs/agents to tissue in the body, the drugs/agents having activity, such as anti-proliferative activity, in the vascular, particularly the endovasculature and more particularly, the cardiovascular system. This invention is useable alone or in conjunction with one or more separate device(s) used to treat medical infirmity or disease. The drugs used in this invention are coated onto a distally disposed, therapy delivery portion or expansion member of a guidewire and are released from the device segment or portion where they are deployed in a short time, preferably less than 10 minutes, more preferably less than 5 minutes, and most preferably 60 seconds or less upon member activation. Drug release or delivery is accomplished, in one embodiment, by radial expansion of a drug-delivering or drug-supporting portion or surface, or expansion member attached to and activated by expansion means of the guidewire within the vasculature, e.g., at the vascular blockage site. Methods of releasing the therapy also can include activating a trigger mechanism, or having the physiological conditions in the body e.g., temperature, pH, ionic balance, etc., trigger the drug release. Other methods and techniques for guidewire-based expansion member activation include torsionally-induced radial expansion of the member, hydraulic expansion, electro-mechanical expansion, use of shape memory materials which "remember" an expanded or collapsed state under defined conditions.

A method of the present invention comprises contacting the tissue or circulation with a radially-expanding guidewire portion, member, or segment which is coated with a therapeutic drug, agent or biological substance, wherein the agent is released into the circulation or deposited onto the tissues surrounding the device in a short time after the contact (or immediately). The therapeutic agent is then quickly, effectively and efficiently absorbed or taken into the tissue, cells or into circulation. The clear and unambiguous, critically important advantage of the guidewire-based approach taken here relative to other endoluminal or endovascular drug delivery approaches is that use of a guidewire expansion member according to this invention provides a minimal diameter "low profile" therapeutic delivery. In practice of this invention precious radial intraluminal or intravascular space or "real estate" (as it is sometimes called) is not occupied with structures such as balloon layers, catheter bodies, sheaths, and other device structural features. In short, the method/delivery of this invention permits access to smaller, more tightly circuitous luminal structures, e.g., of smaller or more highly occluded vessels. It also permits drug delivery without ischemic/schemic effects such as those caused by, for example, vessel blockage with a balloon.

Therapeutic drugs for coating the device include but are not limited to medicines, proteins, adjuvants, lipids and other compounds which ameliorate the tissue or circulation surrounding the device. Additionally, the drug may be encapsulated in particles or controlled release carriers including liposomes, microparticles, and nanoparticles, which are coated upon the device, or bonded to it. Alternatively, the drug may be an aggregate or flocculate of the drug or drug formulation. These drug aggregates are considered a type of particle, as described herein. The therapeutic drug or drug formulation may have sustained anti-proliferative activity and thus a prolonged effect. One example of a group of drugs useful in the present invention to inhibit proliferative activity in the cardiovascular system, specifically smooth muscle cell proliferation, are paclitaxel, sirolimus, everolimus, or ABT-578 biological agents, such as cells and antibodies, could also be used to promote positive tissue growth or inhibit tissue growth or cellular proliferation contributing to or causing restenosis.

The terminology "coated," "coated thereon," "coated onto the guidewire" and common variations thereof is to be broadly interpreted to mean deposited, adhering, locally disposed as well as actually coated onto the operant surface as in the working or expansion surface of a guidewire or a portion thereof. Those terms are intended to include the full spectrum of possible adherent relationships between e.g., the expansion member, and the drug or agent to be delivered. Those terms also include what is primarily a physical interaction, e.g., a drug delivery expansion member or means with a "roughened" surface. "Roughened" textured or porous surface drug retention and subsequent delivery are known in the stent art.

The present invention comprises a substantially cylindrically shaped expansion member deployed by and a part of the distal portion of a guidewire. It includes an expansion means engaged to the expansion member for altering the distance between the proximal end and the distal end of the expansion member thereby transforming the expansion member between a diametrically or radially contracted configuration and a diametrically or radially expanded configuration. A therapeutic agent or medicament can be coated directly onto the expansion member or alternatively, the therapeutic agent or medicament can be incorporated into a polymer or other substrate and then coated on the expansion member.

The present method also comprises the steps of advancing the guidewire including its expansion member e.g., an expandable mesh basket or balloon-like structure, to the obstruction in a vessel and applying opposed forces on said expansion member (e.g., on its distal and proximal ends or portions) in an axial direction to move the expansion member to an expanded configuration wherein the expansion member dilates the obstruction and the catheter/expansion member assembly actively (or passively) delivers the therapeutic agent or medicament to the obstruction. Hydraulic, pneumatic, electrical or electro-mechanical actualizations also are contemplated. Generally speaking this means endovascular deposition of a drug or agent adjacent to or upon a vascular blockage or site of medical interest.

The present method also comprises the steps of advancing its expansion member of the guidewire to e.g., an obstruction in a vessel and applying opposing or opposed forces on said expansion member in an axial or rotational direction to move the expansion member to an expanded configuration wherein the expansion member dilates the obstruction and the guidewire/expansion member assembly actively (or passively) delivers the therapeutic agent or medicament to the obstruction. Opposing forces as used here includes static force, or simply resistance to application of kinetic (moving) force, static force includes, for example, one end of the expansion member being anchored or attached to a guidewire structure which resists axial or rotational movement causing the expansion member to expand.

In yet a further embodiment, the present invention relates to a guidewire having a guidewire expanding member which, in turn has particles dispersed or coated on its surface, each particle encapsulating a therapeutic drug or agent(s), or a combination of therapeutic drugs, having anti-proliferative activity in e.g., the cardiovascular system. The particles may preferably be liposomes, microparticles or nanoparticles. The guidewire expanding member or structure is contacted with surrounding tissue or deployed into circulation such that the therapy is released from the particle and into the surrounding tissue or circulation depending upon the medical problem and/or its treatment.

The method of the invention allows the release of drugs or agent and drug or agent formulations from a low profile guidewire structure i.e., a device, that is not permanently implanted in the body. A "low profile" guidewire as that term is used herein is one in which there is no more than about a 10%, preferably less than about 5%, and most preferable less than about 2% variation in diameter a profile from one end of the device to the other. In other words, essentially the only variation in diameter of this device is the thickness of the drug coating thereon when the guidewire is in the unexpanded, vessel navigation state.

DETAILED DESCRIPTION OF THE INVENTION

Figure 4:
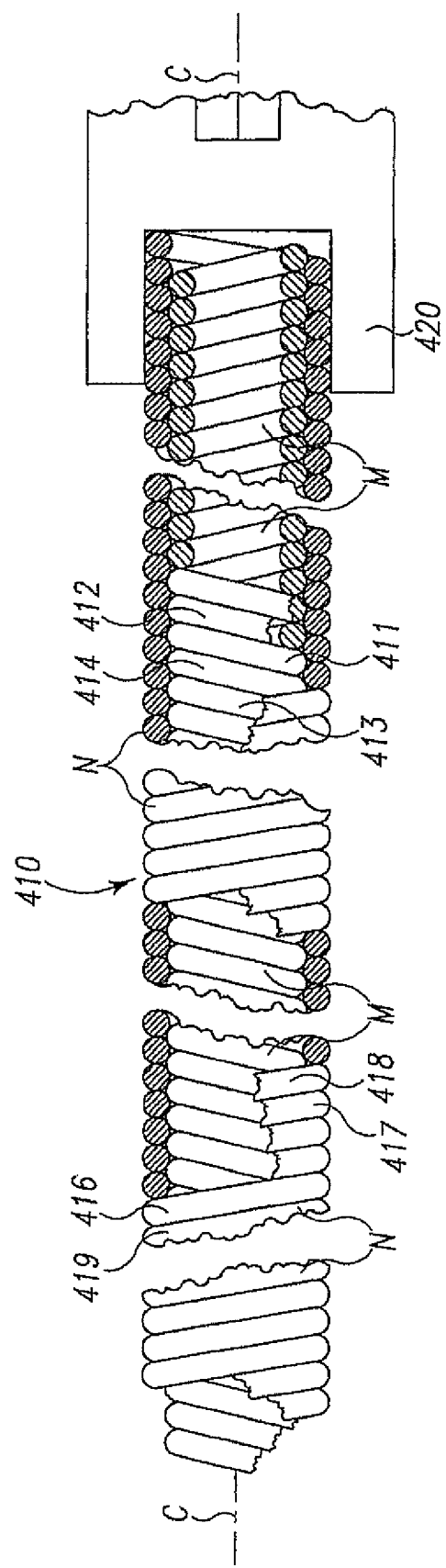
FIG. 4 is in part a side view, in part a cross-sectional view through the outer and inner coils and in part a cross-sectional view through the outer coil and a side view of the inner coil of a cable (sometimes called a torque cable) useable in this invention (e.g., as the expansion means or movement mechanism) and a cross-sectional view through a part of a connector or coupling, a number of axial intermediate parts being broken away (U.S. Pat. No. 5,678,296 to Fleischhacker et al describes this torque cable, the entire disclosure of which is incorporated by reference herein).
Figure 5:
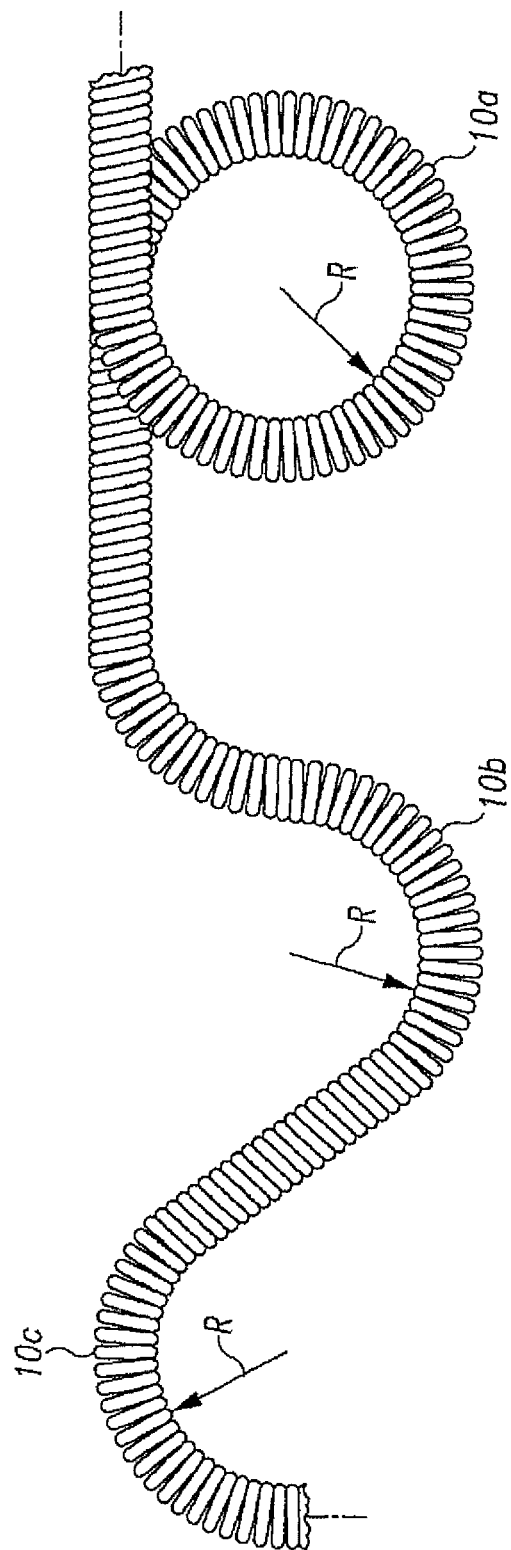
FIG. 5 is a side view of a part of an axial length of a torque cable/expansion means in this invention indicating its flexibility.

The present invention relates to a method of delivering drug(s), agent(s), cells or biological substances (the term "agent" includes drugs, biological substances, and biologics as those terms are used in their arts) in a target-specific manner, through the use of a drug or therapy-coated guidewire segment, portion or member, which includes drug delivery means and guidewire structure. The claimed method provides a therapy that targets the traumatized area by proximity alone or in combination with a systemic effect i.e. delivery from an exterior surface of a guidewire. A drug of the present invention provides, for example, anti-proliferative therapeutic activity to the cardiovascular system. A drug of this invention generally is effective locally, i.e., at the site of vessel contact, but may have more general systemic effects. A drug deployed by means of the present invention does not require a delayed or long-term release and can be used, e.g., to activate anti-proliferative activity immediately upon contact with the cells of the target tissue or circulation. The drug may have sustained anti-proliferative activity and thus, a prolonged effect. The drug is preferably released in less than about or equal to one minute from the time of its initial contact with the tissue or circulation although longer drug release time will often be used depending upon the drug, the specific therapy and related indications and side effects. FIGS. 4 and 5 shown in section an embodiment of this invention in which a monofilament expansion member is used.

The drugs or agents coated upon the guidewire surface, e.g., a radially-expanding surface, and thus useful in the present invention are delivered to the target tissue in a short time after the device's initial contact with the targeted tissue or surrounding circulation, i.e., there is a relatively quick release of the drug from the guidewire to the tissue. The drugs which can be used in the present invention provide, in one approach, anti-proliferative activity in the cardiovascular system. Other agents may promote tissue growth to expedite vessel healing, e.g. anti-h-CO54 antibody.

In one embodiment, the activity of the drug may be sustained, and the drug exhibits a prolonged anti-proliferative effect. Therefore, the drug does not require a delayed or prolonged release and as such, the release can be immediate. Accordingly, the drug may be attached to a working or delivery surface of the device that is not a permanent implant but rather briefly contacts the tissue or circulation. Additionally, due to its sustained effect, the drug may also be encapsulated in a particle which may enhance its uptake by the target tissue or cells.

The drugs may be directly applied to the guidewire expansion member in a composite, wherein the drugs are mixed with other reagents, or may be encapsulated within drug release particles such as liposomes, microparticles, nanoparticles, or aggregates of the drug. The particles may include inert polymeric particles, such as, for example, microparticles or nanoparticles. Alternatively, the particles may comprise biologically derived reagents, such as, for example, lipids, sugars, carbohydrates, proteins and the like. Specifically, such particles are release carriers which provide an effective release of the therapeutic agent to the target tissue or cells. The therapeutic agent formulation may be specifically taken up by cells of the white blood-cell lineage, such as macrophages or monocytes. By this means, the drugs are delivered in a target-specific manner, without the need to provide a full dosage of drugs to the entire body through conventional drug delivery routes as discussed above. Indeed, providing the therapeutic agent in a localized manner or to specific cells can avoid the undesired side effects of such large doses. The drug release carriers are preferably biodegradable, so that when they are brought into contact with the target tissue or circulation or when taken into specific cells, the drug or therapeutic agent is quickly released from the carrier, and then the biodegradable carrier is itself, in due time, removed by natural body processes.

In one embodiment of the present invention the particles or release carriers include, but are not limited to, semi-synthetic polyacryl starch microparticles, other biodegradable microparticles containing the therapeutic agent, ethyl cellulose, poly-L-lactic acid, heptakis (2,6-di-O-ethyl)-beta-cyclodextrin, polyalkylcyanoacrylate nano capsules, polymethylacrylate, monocarboxycellulose, alginic acid, hyaluronic acid, lipid bilayer beads, polyvinylpyrollidone, polyvinyl alcohol, albumin, lipid carriers of continuous phase (non-microparticle type), nanoparticles, and known agents by those skilled in the art for the release of therapeutic agents. Nanoparticles are preferably spherical or non-spherical polymeric particles that are 30-500 nm in diameter.

In a further embodiment of the present invention, the therapeutic agent or drug may be encapsulated within, or form itself, a liposome, colloid, aggregate, particle, flocculate or other such structure known in the art for encapsulation of drugs. The encapsulation material itself may have a known and predetermined rate of biodegradation or bioerosion, such that the rate of release and amount released is a function of the rate of biodegradation or bioerosion of the encapsulation material. Preferably, the encapsulation material should provide a relatively quick release rate.

In yet a further embodiment of the present invention, the particles, or release carriers, may be supported within the matrix of a macrostructure. Particles or controlled release carriers, as previously discussed, include, but are not limited to, microparticles, nanoparticles, colloids, aggregates, liposomes, particles, or flocculates. Materials used to provide the macrostructure include, but are not limited to, fibrin gels, hydrogels, or glucose. Non-limiting examples of particles supported within a macrostructure include a fibrin gel with colloid suspended within it; a hydrogel with liposomes suspended within it; a polymeric macrostructure with macroaggregated albumin suspended within it; glucose with liposomes suspended within it; or any of the foregoing further including liposomes, flocculants microparticles, nanoparticles, or other particles containing or having dispersed therein a drug or therapeutic agent. In the use of this invention it need not be that the macrostructures nor the particles be entirely bioabsorbed. For example if fibrin or collagen is used to provide the macrostructure, such materials are biodegradable yet can persist in the extracellular matrix for substantial lengths of time.

In one embodiment of the invention, the drug or therapeutic agent is encapsulated within liposomes. Liposomes may be submicroscopic, i.e., preferably no greater than 100 nm in size, capsules consisting of a double membrane containing various lipids. One such lipid is a phospholipid, a natural material commonly isolated from soy beans. Liposomes are nontoxic and generally recognized as safe by the FDA. Liposomes can be characterized as a hollow flexible sphere containing an aqueous internal compartment surrounded by an external aqueous compartment. Any material trapped inside the liposome is protected from the external aqueous environment. The lipid bilayer acts as a barrier and limits exchange of materials inside, with materials outside the membrane. Furthermore, the lipid bilayers are hydrophobic and can "entrap" and retain similar types of substances. The rate of release of an encapsulated therapeutic agent or drug from a liposome can be, for example, controlled by varying the fatty acid composition of the phospholipid acyl groups, or by providing elements which are embedded in the lipid bilayers, which specifically allow a controlled and rapid release of the encapsulated drug from the liposomes. In practice, chemical modification of the phospholipid acyl groups is accomplished by either chemically modifying the naturally derived materials, or by selecting the appropriate synthetic phospholipid. The embedded elements in the liposome may be biologically- or bioengineering-derived proteins, polypeptides or other macromolecules to selectively provide pores in the liposome wall.

Liposomes are highly advanced assemblages consisting of concentric closed membranes formed by water-insoluble polar lipids. The lipids comprising the membrane may be selected from the group consisting of natural or synthetic phospholipids, mono-, di-, or triacylglycerols, cardiolipin, phosphatidylglycerol, phosphatidic acid, or analogues thereof. Preferably, the liposome formulations are prepared from a mixture of various lipids.

The natural phospholipids are typically those from animal and plant sources, such as phosphatidylcholine, phosphatidylethanolamine, sphingomyelin, phosphatidylserine, or phosphatidylinositol. Synthetic phospholipids typically are those having identical fatty acid groups, including, but not limited to, dimyristoylphosphatidylcholine, dioleoylphosphatidylcholine, dipalmitoylphosphatidylcholine, distearoylphosphatidylcholine and the corresponding synthetic phosphatidylethanolamines and phosphatidylglycerols.

Other additives such as cholesterol, glycolipids, fatty acids, sphingolipids, prostaglandins, gangliosides, neobee, niosomes, or any other natural or synthetic amphophiles can also be used in liposome formulations, as is conventionally known for the preparation of liposomes.

Stability, rigidity, and permeability of the liposomes are altered by changes in the lipid composition. Membrane fluidity is generally controlled by the composition of the fatty acyl chains of the lipid molecules. The fatty acyl chains can exist in an ordered, rigid state or in a relatively disordered fluid state. Factors affecting rigidity include chain length and degree of saturation of the fatty acyl chains and temperature. Larger chains interact more strongly with each other, so fluidity is greater with shorter chains. Saturated chains are more flexible than unsaturated chains. Transition of the membrane from the rigid to the fluid state occurs as the temperature is raised above the "melting temperature". The melting temperature is a function of the length and degree of unsaturation of the fatty acyl chain. In one embodiment, the liposomes, drug aggregates, microparticles, or nanoparticles are created in a pre-selected size that is preferably taken up by macrophages and monocytes. Thus, the liposomes act within the macrophages to incapacitate them or to inhibit their activity. In a preferred embodiment of the present invention, the liposomes are greater than 100 nm.

In addition to temperature and lipid composition, inclusion of a sterol, such as cholesterol, or a charged amphiphile can alter the stability, rigidity and permeability of the liposome by altering the charge on the surface of the liposome and increasing the distance between the lipid bilayers. Proteins and carbohydrates may be incorporated into the liposomes to further modify their properties. (See U.S. Pat. No. 4,921,757 entitled "System for Delayed and Pulsed Release of Biologically Active Substances," issued May 11, 1990).

The therapeutic agent either directly coated upon or encapsulated and suspended upon a guidewire shall be quickly released into the surrounding tissue or circulation of the cardiovascular system once the guidewire has been implanted or reaches the target area.

Optionally, it may be desirable to position a porous layer over the layer of therapeutic drug coated upon the guidewire or guidewire portion, in order to protect the therapeutic drug from releasing prematurely from the guidewire, that is, prior to reaching its target tissue or circulation. Additionally, the porous layer may also be positioned over the layer of microparticles or nanoparticles encapsulating the therapeutic drug. If utilized, the porous layer is preferably biodegradable and slowly consumed during the insertion or deployment of the guidewire, but can also be an inert stable layer. The thickness and type of material used to construct the porous layer is chosen based on the type of device, the insertion or deployment method used, and the length of time the device is in contact with body fluids prior to reaching its target tissue or circulation. Thus, various devices and applications require porous layers which degrade at different rates. However, most of the porous layer is preferably dissolved by the time the guidewire reaches its target tissue or circulation in order for the therapeutic agent to be quickly and effectively released.

Alternatively, instead of a porous layer deposited over an existing layer of microparticles or nanoparticles, the material of these particles may be selected such that the biodegradation or bioerosion of the encapsulation material occurs at a rate which does not allow the therapeutic agent to be released prematurely.

The release profile of the drug from the microparticles or nanoparticles is determined by many factors including the drug solubility and the thickness and porosity of the microcapsules. The microcapsules of the invention may either be rupturable to release their contents or may be degradable such that they will open when left against the lumen walls. Thus, the particles or capsules may release their contents through diffusion or by rupturing due to the application of external forces. The particles or capsules may also be consumed by the phagocytic, chemotactic, and cytotoxic activities of surrounding cells. For example, macrophages are important killer T-cells and by means of antibody-dependent cell-mediated cytotoxicity (ADCC) they are able to kill or damage extracellular targets. Additionally, the drugs may be released by activating a trigger mechanism, or having it activated passively by the physiological conditions.

In one embodiment of the invention, the drug-coated guidewire expansion member can be configured as at least one of, or any portion of, a catheter, an angioplasty device, a stent, a vascular or other graft, a cardiac pacemaker lead or lead tip, a cardiac defibrillator lead or lead tip, a heart valve, a suture, a needle, a guidewire, a cannula, a pacemaker, a coronary artery bypass graft (CABG), an abdominal aortic aneurysm device (Triple A device) or an orthopedic device, appliance, implant or replacement. In a further embodiment, the guidewire can also be configured as a combination of portions of any of these devices. The drug may be coated on the entire surface of the medial device or a portion thereof. For example, the entire structure may be coated with a type of therapeutic agent, or only a specific portion, which will contact a target area, may be coated.

Figure 1:
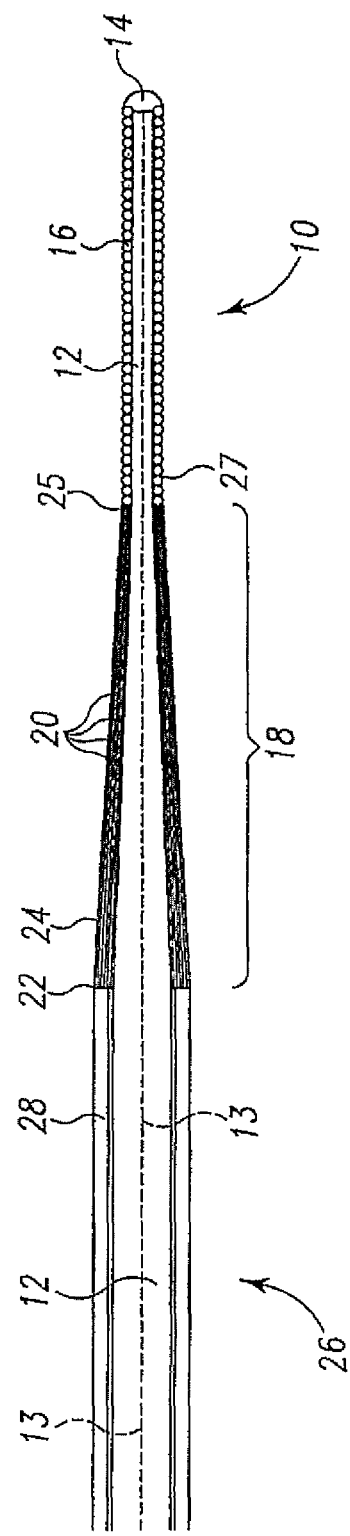
FIG. 1 shows in section a drug delivery guidewire of this invention in navigation to a site of medical interest state.
Figure 2:
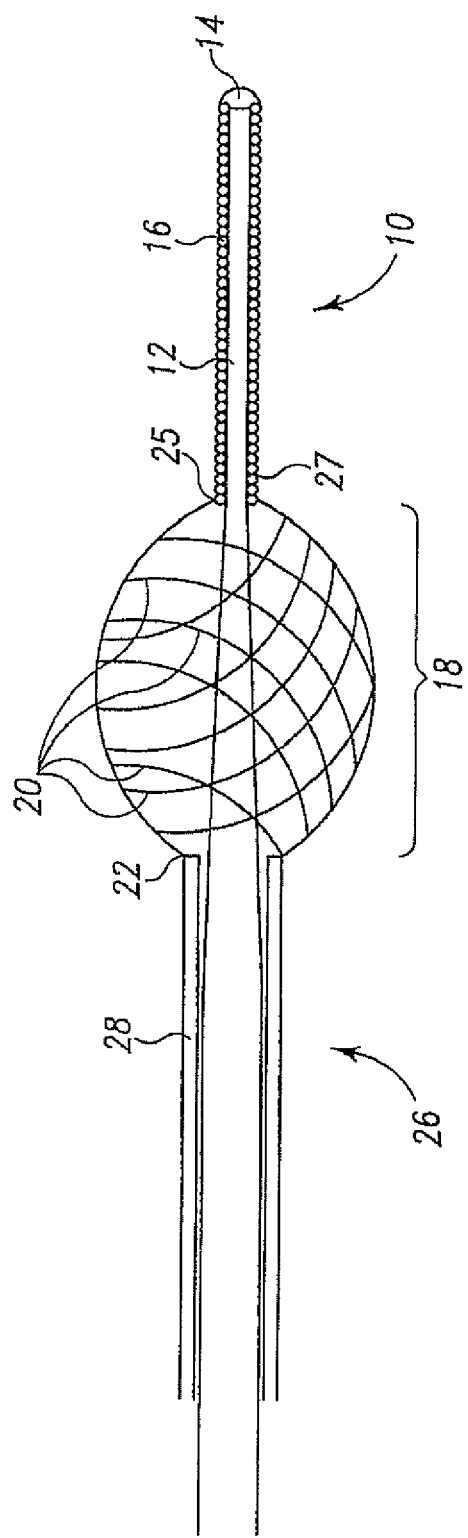
FIG. 2 shows one of the guidewires of FIG. 1 in a drug or agent-deployment or agent delivery state.

Reference now is made to the FIGS. 1-2 in which there is shown a guidewire 10. Guidewire 10 has a central core wire 12 which ends in an atraumatic, bulbous or bullet-shaped tip 14. Proximal to tip 14 is (in this embodiment) a radiopaque coil 16. Coil 16 is connected to central core wire 12 and tip 14 e.g., by soldering adhesives or welding. Proximal to coil 16 is an expansion member 18 which in this example is a series of interwound, (e.g. woven), radially expandable drug-coated struts 20. Struts 20 tend to operate as a unit or member so that application of force to the more proximal end 24 of struts at 22 causes the struts to expand radially outward away from the central axis of core wire 12 generally corresponding to a line down the middle of core wire 12, e.g., dashed line 13 in FIG. 1 and toward, e.g., the inside of a vessel. Force is applied to the more proximal end 24 of woven struts 20 by expansion means 26 which in this embodiment is a substantially longitudinally rigid or "stiff" tubular member 28 which is both "pushable" (or steerable) and "torqueable" as those terms are used in the art. (See, e.g., FIGS. 7 and 8). Various other mechanisms to cause expansion member 18 to expand radially e.g., proximal application of radial torque to a counter-wound, 1:1 torque-transmissive coil, will readily be appreciated by one skilled in this art in light of this disclosure. Tubular member 28 has an inside diameter which is just sufficiently larger than the outside diameter of core wire 12 so as to slidably engorge therewith. It will be appreciated that tubular member 28 will have substantially the same rigidity and steerability as core wire 12 so as to cooperate therewith while the guidewire 10 is being directed into the vasculature. Application of distally-directed force to tubular member 28 causes expansion member 18 to expand radially and hence to deploy drug or agent (not shown) coated thereon into and onto the endovasculature, its distal end 25 being held in place by the proximal end 27 of radiopaque coil 16.

FIG. 1 is generally the configuration of guidewire 10 of this embodiment of the invention during navigation of the guidewire to and through the vessel site to be treated.

FIG. 2 shows the configuration of guidewire 10 with expansion member 18 in its expanded or delivery state 18. Proximal retraction of tubular member 28 will cause expansion member 18, i.e., the strut structure, radially to contract so as to return generally to its navigation configuration and for further proximal withdrawal of guidewire 10. During the expanded state, expansion means or member 26 delivers drug or agent to the site of medical interest, the drug or agent being chosen to address the medical issue e.g., blockage, restenosis, inflammation, which makes the deployments site medically of interest. Expansion member 26 may have an inherent tendency or bias to return to its non-expanded, navigation state. Whether an expansion member does or does not have a tendency to return to a smaller diameter will determine how affirmatively tubular member 28 is attached to the proximal end of expansion member 26 as well as to the structure on its distal end.

Figure 3:
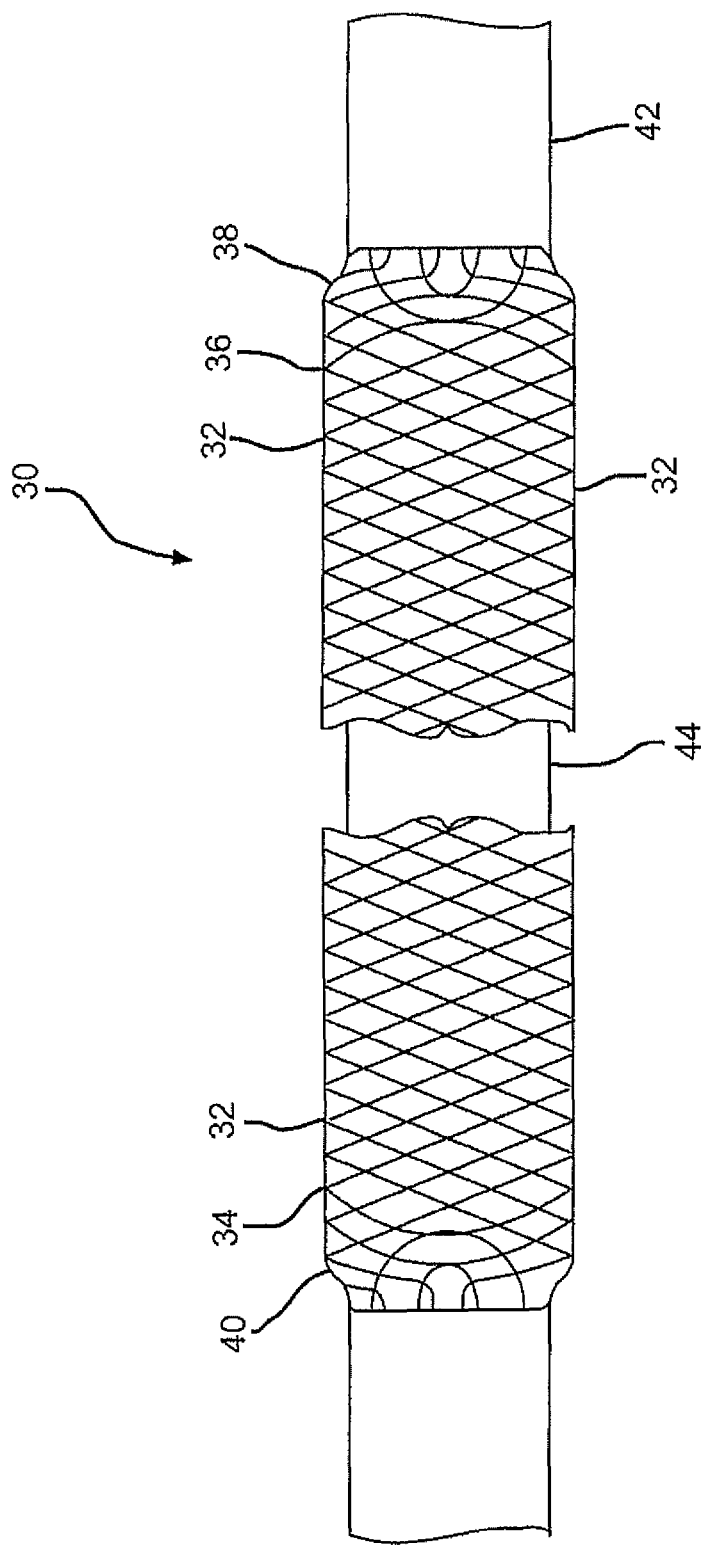
FIG. 3 is a second embodiment of an expansion member of this invention.

FIG. 3 is a second embodiment of a guidewire expansion member 30 of this invention. Expansion member 30 is a mesh or woven cylindrical structure comprising individual woven or overlapping struts, strands, helices or wires 32. Member 30 has a distal end 34 and a proximal end 36 (physician's frame of reference). Proximal end 36 of mesh expansion member 30 has a shoulder or ridge 38 as does distal end 34 (at 40). In this variation expansion member 30 is attached to expansion means 42 which, as above, is a hollow flexible tubular member. Expansion member 30 is basket-like, bulbous or prolate comprising interwoven strands tending to act like an integrated unit or entity. Expansion member 30 slidably engages guidewire core wire 44. Distal end 34 of mesh structure 32 is affixed to guidewire 44. Application of distal force to tubular member 42 causes mesh structure 32 to expand radially and deliver endovascularly any drug or agent (not shown) disposed thereon. Similarly, the expansion member could be a distal coil, segment, or portion (not shown) that expands and contracts radially as rotational and/or translational force is applied to its proximal end or segment.

Referring to FIG. 4, a torque cable useable in this invention, generally designated 410, includes an inner coil M made up of a single layer of multifilar helically wound coil of wires, preferably four wires 411, 412, 413, and 414 that has each convolution (helix) of one wire in contact with the adjacent convolution of two other wires. While a multifilar torque cable is preferred, monofilar coils (i.e., a single helically-wound wire) are also contemplated. The inner coil is wound to be, in a relaxed non-assembled condition, a coil having an inner peripheral diameter W and a coil outer peripheral diameter Z. The cable 410 also includes an outer coil N made up of a single layer of multifilar helically wound coil of wire, preferably four wires 416, 417, 418, and 419 that are wound in the opposite direction from the winding of the inner coil, and likewise has adjacent wire convolutions in contact with one another. The outer coil is wound in a relaxed non-assembled condition having a coil inner peripheral diameter X and a coil outer peripheral diameter Y. For example, the inner coil outer peripheral diameter in a non-(W) assembled condition may be about 0.002" greater than the outer coil inner peripheral diameter in a non-assembled condition (X). The torque cable discussed herein could also be used with or coupled to tubular member 28 to comprise an expansion means as that term is used herein. The torque cable could also be coupled to a distal coil segment as is discussed in the previous paragraph.

In order to assemble the torque cable, the outer coil is partially unwound by applying an unwinding force to increase the coil inner peripheral diameter. Then the inner coil is inserted into the partially unwound outer coil and thence the unwinding force that was applied to the outer coil is released. The axial central part of the outer coil starts to shrink first to form an interference fit with the inner coil and continues to shrink its outer coil diameter toward the outer coil opposite ends whereby there is obtained an interference fit throughout the entire axial length of the cable. All of the helices of each of the coils in the assembled condition of the coils are of substantially the same inner and outer diameters throughout the axial lengths of the coils while the inner and outer coils are of substantially the same axial lengths. That is the helices of each coil are of substantially the same radial spacing from the respective coil central axis C-C.

By assembling through partially unwinding the outer coil and allowing it to contract after the inner coil has been inserted, the cable 410 may by made of an outer diameter of about 1/16" or less and bent through, for example, a circular configuration portion 10a of a radius of curvature R of, for example about 1" or/and "S" curved portions 10b, 10c radii of curvature such as illustrated in FIG. 5.

Figure 6:
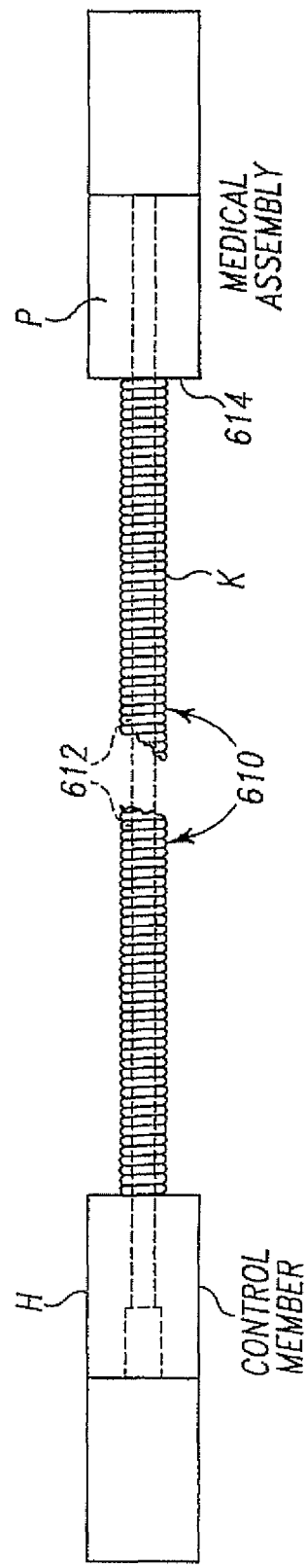
FIG. 6 is a side view of manually operated medical apparatus that includes a control member, a medical subassembly, and the torque cable coupling or connecting with nearly 1:1 torque transmission, the control member and medical subassembly being diagrammatically illustrated.

Referring to FIG. 6, the medical apparatus K includes a cable 610 that has its proximal end portion fixedly attached to an optional manually operated control member H while the distal end portion mounts and couples to a medical subassembly P, the control member and medical subassembly being diagrammatically illustrated. Medical subassembly 2, in this embodiment of the invention is e.g., a guidewire expansion member portion, segment, or working surface according to this invention. (Guidewire core wire 612 is shown and designated by broken lines). For example, expansion member P would comprise a woven structure, basket, bulbous member, which when torque was applied to central member H, would be transmitted on a substantially 1:1 basis by counter-wound torque cable 610 to the proximal end 614 of subassembly P and cause the subassembly P (the distal end of subassembly P presumably being anchored e.g., at the guidewire tip (not shown)) to expand radially. Agent coated on subassembly/expansion member 9 would then be endovascularly delivered either locally or systemically.

Figure 7:
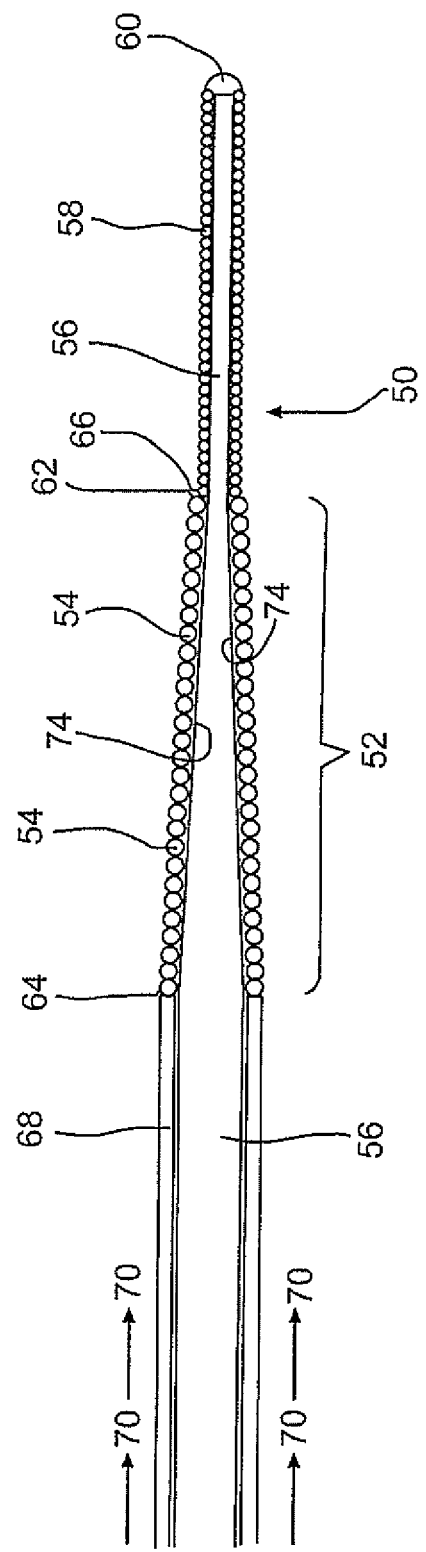
FIGS. 7 and 8 show in section an embodiment of this invention in which a monofilament expansion member is displayed on the distal end, portion or segment of a guidewire.
Figure 8:
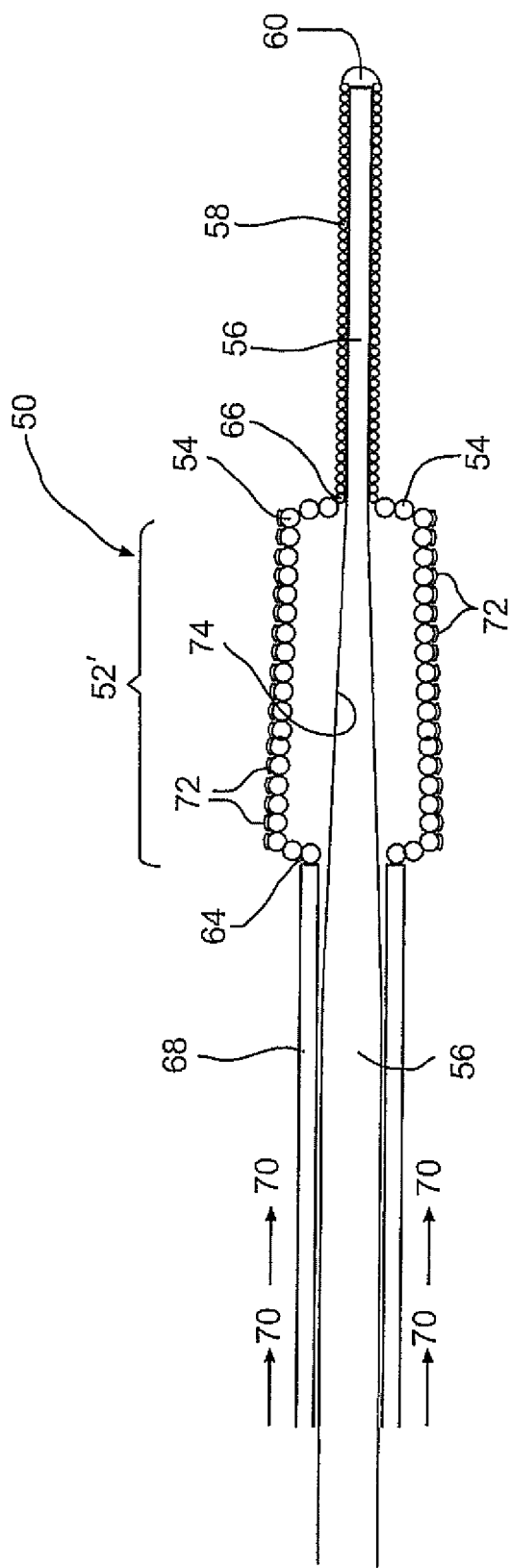

FIGS. 7 and 8 illustrate in section a further embodiment of the present invention. FIG. 7 depicts the device in its vascular navigation stage while FIG. 8 shows the device in its drug delivery stage.

In FIG. 7 the guidewire 50 includes an expansion member 52 which comprises a single helically-wound filament or wire 54. Multi-filar expansion members also could be used.

Guidewire 40 comprises a core wire 56 and a radiopaque coil 58. Core wire 56 and radiopaque coil 58 are coupled to each other e.g., by solder, spot weld or adhesive, at distally-extreme, atraumatic tip 60.

Expansion member 52 has a distal end or portion 62 and a proximal end or portion 64. As is shown expansion member distal end 62 abuts radiopaque coil 58 at the coil's proximal end 66 and is thereto affixed to core wire 56. Expansion means or torsion mechanism 68 is, in this embodiment, a hypotube segment having an inside diameter which is about the same as, but slightly larger, than the outside diameter of guidewire core wire 56 at its proximal length. Hypotube 68 is substantially longitudinally or torsionally rigid such that proximally applied, torque or distally-directed force (e.g., arrow 70) is efficiently transmitted to expansion member 52 proximal end 64.

FIG. 8 shows the guidewire of FIG. 7 as it appears when member 52' is in the expanded state, e.g., when delivering a drug or agent endovascularly, alone or in conjunction with a luminal opening and expansion of a vessel. Drug or agent (not shown) is or would be coated at least on the outermost segment 72 (only shown in FIG. 8) of filament or wire 54. (Filaments 54 could also be completely coated with drug, agent, or biologic). Expansion member 52', in this embodiment, is shown to be substantially conical with a slightly distally decreasing, outward diameter. As in the earlier embodiments, expansion member 52, 52' is disposed along and is collinear with core wire and tapers in parallel with taper 74. Outside segments 72 are shown to be substantially planar. Such a configuration could be obtained e.g., by differential tempering or treating of individual expansion member helices 54. In this manner overall guidewire outside diameter is kept to a minimum even during drug delivery and/or concurrent or separate vessel angioplasty.

In a preferred embodiment, a drug-coated or drug bound guidewire, working surface or guidewire portion (usually but not necessarily an expansion member) is utilized to release the therapeutic agents having anti-proliferative activity into the body tissue or circulation.

The therapeutic agent, preferably encapsulated in a particle or a controlled release carrier, or aggregated to a desirable/pre-selected size, for efficient uptake by a macrophage, is applied to the surface of the guidewire by coating methods known in the art, including, but not limited to spraying, dipping, rolling, brushing, solvent bonding, adhesives or welding or by binding the microparticle or aggregates to the surface of the guidewire by any chemical method known in the art. Furthermore, if the guidewire has folds, corrugations, cusps, pores, apertures, or the like, the therapeutic agent or particle encapsulating the therapeutic agent may be embedded, i.e., mechanically trapped, within the guidewire without the use of adhesives. In addition to the drug coated on the guidewire, an additional dosage of the therapeutic drug, which inhibits proliferation in the cardiovascular system, may be applied by conventional delivery methods discussed above, (e.g., orally, intravenously) or may be injected through the guidewire. For example, the therapeutic drug may be injected through the guiding catheter via the same method and procedure used to inject the contrast dye commonly used during a PTA. The particles are preferably selected from the group consisting of lipids, microparticles, nanoparticles, or the drug itself in aggregates, flocculates or the like.

The therapeutic drugs useful in the present invention preferably inhibit the proliferation of vascular smooth muscle cells. In one embodiment, the therapeutic drugs directly alter smooth muscle cell activity by altering cellular metabolism, inhibiting protein synthesis, or inhibiting microtubule and microfilament formation, thus affecting morphology. The therapeutic drug may also include inhibitors of extracellular matrix synthesis or secretion. Thus, in one embodiment, the methods and dosage forms of the present invention are useful for inhibiting vascular smooth muscle cells by employing a therapeutic agent that inhibits the activity of the cell, i.e. inhibits proliferation, contraction, migration or the like, but does not kill the cell. However, in a further embodiment, the methods and dosage forms of the present invention are useful for inhibiting target cell proliferation by employing a therapeutic agent that is cytotoxic to the cell.

The therapeutic agent, may directly or indirectly inhibit the activity of the smooth muscle cells, thus inhibiting or suppressing proliferation of the smooth muscle cells. For example, in one embodiment, the therapeutic agent may directly inhibit the cellular activity of the smooth muscle by inhibiting proliferation, migration, etc. of the smooth muscle cells. In a further embodiment, the therapeutic agent may inhibit the cellular activity of surrounding cells, whose activity initiates, assists or maintains proliferation of smooth muscle cells. Thus, smooth muscle cell proliferation is indirectly inhibited or suppressed by the inhibition or suppression of the metabolic activities of the surrounding cells, whose activities maintain smooth muscle cell proliferation.

In a preferred embodiment, the therapeutic drug encapsulated and coated on the guidewire is used for reducing, delaying or eliminating restenosis following angioplasty. Reducing restenosis includes decreasing the thickening of the inner blood vessel lining that result from stimulation of smooth muscle cell proliferation following angioplasty. Delaying restenosis includes delaying the time until onset of visible hyperplasia following angioplasty, and eliminating restenosis following angioplasty includes completely reducing and/or completely delaying hyperplasia to an extent which makes it no longer necessary to intervene. Methods of intervening include re-establishing a suitable blood flow through the vessel by methods such as, for example, repeat angioplasty and/or stent placement, or CABG.

One example of a group of drugs useful in the present invention to inhibit proliferative activity in the cardiovascular system, specifically smooth muscle cell proliferation, are bisphosphonates (BP). Bisphosphonates, formerly called diphosphonates, are compounds characterized by two C—P bonds. If the two bonds are located on the same carbon atom (P—C—P) they are termed geminal bisphosphonates. Bisphosphonates indirectly inhibit smooth muscle cell proliferation by metabolically altering surrounding cells, namely macrophages and/or monocytes. Bisphosphonates when encapsulated in liposomes or nanoparticles or aggregated in aggregates of a specific size, are taken-up, by way of phagocytosis, very efficiently by the macrophages and monocytes. Once inside the macrophages, the liposomes are destroyed and release the encapsulated bisphosphonates, which inhibit the activity of the macrophages. Since macrophages, in their normal state, are recruited to the areas traumatized by angioplasty or other intrusive intervention and initiate the proliferation of smooth-muscle cells (SMC), inhibiting the macrophages' activity will inhibit the proliferation of SMC. Once released and taken-up by the macrophages, the bisphosphonates will have a sustained antiproliferative activity for the lifetime of the macrophages. Thus, prolonged release of the bisphosphonates is not required in order to sustain inhibition. Representative examples of bisphosphonates suitable for use in the present invention are alendronate, clodronate, and pamidronate.

In a preferred embodiment of the present invention, the therapeutic drug is encapsulated in relatively large liposomes that are preferably taken up by cells such as monocytes and macrophages. The structure and composition of the liposomes are discussed supra. Additionally, the liposomes may be greater than 100 nanometers in size and contain, for example, a bisphosphonate drug.

In one embodiment, the drug, such as, for example, a bisphosphonate may be encapsulated in a liposome and coated upon a suitable guidewire. Coating methods and suitable guidewires are discussed supra. For example, the liposomal bisphosphonates may be coated on a balloon catheter and suspended in a macrostructure such as glucose or gelatin, or chemically bound to the surface. Thereafter, the balloon catheter is effectively maneuvered through the cardiovascular system and to an occlusive site. Once in the proper position, the balloon is inflated into contact with the lumen to be treated. The liposomes, which encapsulate the bisphosphonate therapeutic drugs, are then released from the guidewire and are present in the tissue and in the circulation, ready for uptake by macrophages, locally and systemically.

Upon the release of the liposomes into the lumen of the affected area and immediate uptake by the macrophages, restenosis is inhibited. For example, bisphosphonates may prevent monocytes from developing into macrophages by altering their cellular metabolism. Furthermore, the BP may also inhibit cellular activity of macrophages thereby altering their biological function as the central effector and regulatory cell of the inflammatory response. Therefore, while macrophages are recruited to the traumatized area, these cells can not initiate the inflammatory process that turns into restenosis. The release of the Liposomal BP (LBP) can be carried out systemically and/or locally, and is taken-up by macrophages systemically and locally.

The therapeutic agent may also promote the growth of smooth muscle cells (c.s. anti-h-CO54 antibody or stem cells), which promotes tissue growth and healing to prevent an inflammatory and/or thrombogenic-based restenosis.

In a further embodiment, the guidewire may also carry therapeutic agents, such as, for example, anti-spasmodic, anti-thrombogenic, and anti-platelet agents, antibiotics, steroids, and the like, in conjunction with the anti-proliferative agent, to provide local administration of additional medication.

It is to be understood that the embodiments and variations shown and described herein are merely illustrative of the principles of the present invention. Therefore, various adaptations and modifications may be implemented by those skilled in the art without departing from the spirit and scope of the present invention.

What is claimed is:
1. A guidewire, comprising:
a) an inner helically wound coil extending along a longitudinal axis from an inner helically wound coil proximal portion to an inner helically wound coil distal portion having an inner helically wound coil distal end;
b) a distal atraumatic tip connected to the inner helically wound coil distal end;

c) an outer helically wound coil in an interference fit contact with the inner helically wound coil and extending along the longitudinal axis from an outer helically wound coil proximal end to an outer helically wound coil distal portion having an outer helically wound coil distal end, wherein the inner helically wound coil is wound in a first helically wound direction about the longitudinal axis and the outer helically wound coil is wound in a second, opposite helically wound direction; and d) a tubular member movably supported on the inner helically wound coil proximal portion, the tubular member extending from a tubular member proximal portion to a tubular member distal end, wherein the tubular member distal end is connected to the outer helically wound coil proximal end, e) wherein torsional manipulation of the tubular member in a first rotational direction about the longitudinal axis causes the outer helically wound coil to rotate in the first rotational direction, opposite the second, opposite helically wound direction, to thereby cause the outer helically wound coil to unwind from an unexpanded state in the interference fit contact with the inner helically wound coil to an expanded state spaced further from the longitudinal axis than when in the unexpanded state and at least partially removed from the interference fit contact with the inner helically wound coil, and f) wherein torsional manipulation of the tubular member in a second rotational direction causes the outer helically wound coil to rotate in the second rotational direction, opposite the first rotational direction, to thereby cause the outer helically wound coil to wind back to the unexpanded state in the interference fit contact with the inner helically wound coil.

2. The guidewire of claim 1, wherein the inner helically wound coil wound in the first helically wound direction about the longitudinal axis and the outer helically wound coil wound in the second, opposite helically wound direction provide substantially 1:1 torque-transmission.

3. The guidewire of claim 1, wherein the inner helically wound coil comprises from one to four helical filars.

4. The guidewire of claim 1, wherein the outer helically wound coil comprises from one to four helical filars.

5. The guidewire of claim 1, further including a therapeutic agent or drug coated on the outer helically wound coil.

6. The guidewire of claim 5, wherein the therapeutic agent or drug is selected from the group of paclitaxel, sirolimus, everolimus, ABT-578 biological agents, and mixtures thereof.

7. The guidewire of claim 5, wherein the therapeutic agent or drug is encapsulated within a liposome.

8. The guidewire of claim 7, wherein the liposome is no greater than 100 nm in size.

9. The guidewire of claim 5, wherein the therapeutic agent or drug is mixed with a release carrier selected from the group of semi-synthetic polyacryl starch microparticles, ethyl cellulose, poly-L-lactic acid, heptakis (2,6-di-O-ethyl)-beta-cyclodextrin, polyalkylcyanoacrylate nano capsules, polymethylacrylate, monocarboxycellulose, alginic acid, hyaluronic acid, lipid bilayer beads, polyvinylpyrrolidone, polyvinyl alcohol, albumin, lipid carriers of continuous phase (non-microparticle type), and spherical or non-spherical polymeric nanoparticles from 30 nm to 500 nm in diameter.

10. The guidewire of claim 5, wherein the therapeutic agent or drug is mixed with a release carrier that is selected from the group of fibrin gels, hydrogels, and glucose.

11. The guidewire of claim 5, wherein a biodegradable porous layer is positioned over the therapeutic agent or drug coated on the outer helically wound coil.

12. The guidewire of claim 5, wherein the therapeutic agent or drug is releasable from the outer helically wound coil upon the guidewire having been inserted into a vasculature of a patient for a period ranging from about 60 second to less than 10 minutes.

13. A guidewire, comprising:
a) an inner helically wound coil comprising from one to four wires extending along a longitudinal axis from an inner helically wound coil proximal portion to an inner helically wound coil distal portion having an inner helically wound coil distal end;
b) a distal atraumatic tip connected to the inner helically wound coil distal end;
c) a radiopaque coil supported on the inner helically wound coil distal portion;
d) an outer helically wound coil in an interference fit contact with the inner helically wound coil and comprising from one to four wires extending along the longitudinal axis from an outer helically wound coil proximal end to an outer helically wound coil distal portion having an outer helically wound coil distal end, wherein the inner helically wound coil is wound in a first helically wound direction about the longitudinal axis and the outer helically wound coil is wound in a second, opposite helically wound direction; and
e) a tubular member movably supported on the inner helically wound coil proximal portion, the tubular member extending from a tubular member proximal portion to a tubular member distal end, wherein the tubular member distal end is connected to the outer helically wound coil proximal end,
f) wherein torsional manipulation of the tubular member in a first rotational direction about the longitudinal axis causes the outer helically wound coil to rotate in the first rotational direction, opposite the second, opposite helically wound direction, to thereby cause the outer helically wound coil to unwind from an unexpanded state in the interference fit contact with the inner helically wound coil to an expanded state spaced further from the longitudinal axis than when in the unexpanded state and at least partially removed from the interference fit contact with the inner helically wound coil, and
g) wherein torsional manipulation of the tubular member in a second rotational direction causes the outer helically wound coil to rotate in the second rotational direction, opposite the first rotational direction, to thereby cause the outer helically wound coil to wind back to the unexpanded state in the interference fit contact with the inner helically wound coil.

14. The guidewire of claim 13, wherein the inner helically wound coil wound in the first helically wound direction about the longitudinal axis and the outer helically wound coil wound in the second, opposite helically wound direction provide substantially 1:1 torque-transmission.

15. The guidewire of claim 13, wherein each convolution of one of the one to four wires of the inner helically wound coil is in direct contact with adjacent convolutions of two other wires of the one to four wires of the inner helically wound coil.

16. The guidewire of claim 13, wherein each convolution of one of the one to four wires of the outer helically wound coil is in direct contact with adjacent convolutions of two other wires of the one to four wires of the outer helically wound coil.

17. The guidewire of claim 13, further including a therapeutic agent or drug coated on the outer helically wound coil.

18. A guidewire, comprising:
a) an inner helically wound coil comprising one wire extending along a longitudinal axis from an inner helically wound coil proximal portion to an inner helically wound coil distal portion having an inner helically wound coil distal end;
b) a distal atraumatic tip connected to the inner helically wound coil distal end; and
c) an outer helically wound coil in an interference fit contact with the inner helically wound coil and comprising one wire extending along the longitudinal axis from an outer helically wound coil proximal end to an outer helically wound coil distal portion having an outer helically wound coil distal end, wherein the inner helically wound coil is wound in a first helically wound direction about the longitudinal axis and the outer helically wound coil is wound in a second, opposite helically wound direction,
d) wherein torsional manipulation of the outer helically wound coil in a first rotational direction about the longitudinal axis causes the outer helically wound coil to unwind from an unexpanded state in the interference fit contact with the inner helically wound coil to an expanded state spaced further from the longitudinal axis than when in the unexpanded state and at least partially removed from the interference fit contact with the inner helically wound coil, and
e) wherein torsional manipulation of the outer helically wound coil in a second rotational direction, opposite the first rotational direction, causes the outer helically wound coil to wind back to the unexpanded state in the interference fit contact with the inner helically wound coil.

19. The guidewire of claim 18, wherein the inner helically wound coil wound in the first helically wound direction about the longitudinal axis and the outer helically wound coil wound in the second, opposite helically wound direction provide substantially 1:1 torque-transmission.

20. The guidewire of claim 18, further including a therapeutic agent or drug coated on the outer helically wound coil.

* * * * *